(12) United States Patent
Jaeger et al.

(10) Patent No.: US 6,402,055 B1
(45) Date of Patent: Jun. 11, 2002

(54) DEVICE FOR PRODUCING HIGH PRESSURE IN A FLUID IN MINIATURE

(75) Inventors: Joachim Jaeger, Bruchsal; Pasquale Cirillo, Dortmund; Joachim Eicher, Dortmund; Johannes Geser, Dortmund; Bernhard Freund, Gau-Algesheim; Bernd Zierenberg, Bingen am Rhein, all of (DE)

(73) Assignee: Boehringer Ingelheim GmbH (DE)

( * ) Notice: Subject to any disclaimer, the term of this patent is extended or adjusted under 35 U.S.C. 154(b) by 0 days.

(21) Appl. No.: 09/354,663

(22) Filed: Jul. 16, 1999

Related U.S. Application Data (62) Division of application No. 08/726,219, filed on Oct. 4, 1996, now Pat. No. 5,964,416.

(30) Foreign Application Priority Data

Oct. 4, 1995 (DE) .......................................... 195 36 902

(51) Int. Cl.[7] .............................................. B05B 9/043
(52) U.S. Cl. ........................ 239/333; 239/349; 239/583; 222/383.1; 222/385; 222/401; 137/533; 137/533.17
(58) Field of Search ................................ 239/302, 349, 239/355, 357–363, 333, 337, 338, 583; 222/373, 379, 383.1, 385, 401, 402; 137/533.17, 533.31, 533, 533.11, 220, 532

(56) References Cited

U.S. PATENT DOCUMENTS

| | | | |
|---|---|---|---|
| 362,678 A | * | 5/1887 | Sutton ........................ 137/533 |
| 1,035,261 A | | 8/1912 | Strumpf |
| 2,322,913 A | | 6/1943 | Best et al. |
| 2,550,840 A | | 5/1951 | Martin et al. |
| 3,317,002 A | | 5/1967 | McKenzie |
| 3,319,894 A | | 5/1967 | Cooprider |
| 3,361,069 A | | 1/1968 | Long |
| 3,396,874 A | | 8/1968 | Malone |
| 3,471,065 A | | 10/1969 | Malone |
| 3,575,322 A | | 4/1971 | Jordan et al. |
| 3,605,738 A | | 9/1971 | Ciranna |
| 3,746,251 A | | 7/1973 | Nozawa et al. |
| 3,790,034 A | | 2/1974 | Horvath |
| 3,792,800 A | | 2/1974 | Capra et al. |
| 3,797,748 A | | 3/1974 | Nozawa et al. |
| 3,818,908 A | | 6/1974 | Phillips |
| 3,838,686 A | | 10/1974 | Szekeley |
| 3,878,973 A | | 4/1975 | Riccio |
| 3,901,414 A | | 8/1975 | Capra et al. |
| 3,933,279 A | | 1/1976 | Maier |
| 4,138,039 A | | 2/1979 | Micallef |

(List continued on next page.)

FOREIGN PATENT DOCUMENTS

| | | |
|---|---|---|
| AT | 52014 | 2/1912 |
| CA | 2017366 | 11/1990 |
| DE | 1945257 | 3/1970 |

(List continued on next page.)

OTHER PUBLICATIONS

V.A.W. Hillier and F. Puttuck, fundamental of Motor Vehicle Technology, 3rd Edition, pp. 208–209. (undated).

Primary Examiner—Steven J. Ganey
(74) Attorney, Agent, or Firm—Sterne, Kessler, Goldstein & Fox P.L.L.C.

(57) ABSTRACT

A miniaturized device for pressurizing fluid. The device includes a hollow piston that provides a fluid path and a valve member. The valve member is configured for axial movement so that the valve axis remains parallel to the piston axis. The valve member is arranged at one end of the hollow piston. The valve member may be partially or completely disposed within the hollow piston. The device is particularly adapted for use in a mechanically operated atomizer to produce an inhalable aerosol of a liquid medicament without the use of propellant gas.

15 Claims, 8 Drawing Sheets

U.S. PATENT DOCUMENTS

| | | |
|---|---|---|
| 4,147,476 A | 4/1979 | Warren |
| 4,174,055 A | 11/1979 | Capra et al. |
| 4,183,449 A | 1/1980 | Blake |
| 4,260,082 A | 4/1981 | Rooney et al. |
| 4,264,037 A | 4/1981 | Nazawa |
| 4,271,875 A | 6/1981 | Meshberg |
| 4,345,718 A | 8/1982 | Horvath |
| 4,391,620 A | 7/1983 | Geisel |
| 4,402,432 A | 9/1983 | Corsette |
| 4,414,972 A | 11/1983 | Young et al. |
| 4,441,634 A | 4/1984 | Meshberg |
| 4,602,726 A | 7/1986 | Goda |
| 4,623,337 A | 11/1986 | Maurice |
| 4,693,675 A | 9/1987 | Venus, Jr. |
| 4,694,977 A | 9/1987 | Graf et al. |
| 4,819,834 A | 4/1989 | Thiel |
| 4,867,347 A | 9/1989 | Wass et al. |
| 4,875,605 A | 10/1989 | Weston |
| 4,892,232 A | 1/1990 | Martin |
| 4,896,832 A | 1/1990 | Howlett |
| 5,161,574 A | 11/1992 | Chacin et al. |
| 5,215,443 A | 6/1993 | Hani et al. |
| 5,310,092 A | 5/1994 | Targell |
| 5,316,135 A | 5/1994 | Kneer et al. |
| 5,402,943 A | 4/1995 | King et al. |
| 5,405,084 A | 4/1995 | Weston et al. |
| 5,472,143 A | 12/1995 | Bartels et al. |
| 5,497,944 A | 3/1996 | Weston et al. |
| 5,503,306 A | 4/1996 | Knickerbocker |
| 5,505,343 A | 4/1996 | Knickerbocker |
| 5,547,094 A | 8/1996 | Bartels et al. |

FOREIGN PATENT DOCUMENTS

| | | |
|---|---|---|
| DE | 1653517 | 8/1971 |
| DE | 42 22 732 | 3/1993 |
| EP | 0086144 | 8/1983 |
| EP | 0111875 | 6/1984 |
| EP | 0520571 | 12/1992 |
| FR | 2699390 | 6/1994 |
| GB | 224531 | 10/1925 |
| GB | 310818 | 6/1930 |
| GB | 1014685 | 12/1965 |
| GB | 1100024 | 1/1968 |
| GB | 1131918 | 10/1968 |
| GB | 1140422 | 1/1969 |
| GB | 1202430 | 8/1970 |
| GB | 1239855 | 7/1971 |
| GB | 1279797 | 6/1972 |
| GB | 1291367 | 10/1972 |
| GB | 1350797 | 4/1974 |
| GB | 1389702 | 4/1975 |
| GB | 1493614 | 11/1977 |
| GB | 2243880 | 11/1991 |
| GB | 2291135 | 1/1996 |
| HU | 158889 | 12/1970 |
| HU | 181864 | 6/1977 |
| HU | 184 538 | 9/1983 |
| WO | WO 87/04373 | 7/1987 |
| WO | WO 89/07244 | 8/1989 |
| WO | WO 91/14468 | 10/1991 |
| WO | WO 91/16993 | 11/1991 |
| WO | WO 96/06011 | 2/1996 |

\* cited by examiner

DEVICE FOR PRODUCING HIGH PRESSURE IN A FLUID IN MINIATURE

REFERENCE TO RELATED APPLICATION

This application is a Divisional of application Ser. No. 08/726,219; filed Oct. 4, 1996, now U.S. Pat. No. 5,964,416 the disclosure of which is incorporated in its entirety by reference hereto.

The invention relates to a device for producing high pressure in a fluid. It comprises a piston which is movable in a cylinder, and a valve, both preferably of miniaturised construction. The invention further relates to a high pressure atomiser which contains this device, and the use thereof, preferably for medicinal purposes.

One aim of the invention is to enable a device of this kind and the atomiser containing the device to be made simpler in design and cheaper to produce and suited to its function.

In liquid chromatography (HPLC), for example generally relatively small quantities of liquid are conveyed at high pressure through the separating column. Moreover, in medicinal aerosol therapy, aerosols are obtained, by atomising or nebulising liquid drugs for treating disease of the respiratory tract in humans or for treating asthmatic conditions. Here again, a high pressure is required in a, generally relatively small, quantity of fluid in order to produce the small droplet size needed for the aerosol. In the metered dose inhaler according to U.S. Pat. No. 5,497,944, (the entire contents of which are incorporated herein by reference) a predetermined volume of a fluid is sprayed through a nozzle with a small aperture under a pressure of between 5 and 40 MPa (about 50 to 400 bar) to produce an aerosol. The present invention is particularly applicable to such metered dose inhalers and similar devices.

According to one aspect of the invention there is provided a device, preferably of miniaturised construction, for producing high pressure in a fluid, comprising a piston which is movable in a cylinder, a high pressure chamber which is located in front of the piston inside the cylinder, and a valve, which device includes

- a cylindrical hollow piston,
- a valve member which is guided by the hollow piston and is mounted so as to be axially movable against the hollow piston,
- a stop means on the hollow piston which holds the valve member to the hollow piston and
- a defined (predetermined) sealing surface at the inlet end of the valve member, the valve member generally being restrained from rotation about any axis transverse to the piston axis.

According to another asp of the invention, there is provided a device for producing high pressure in a fluid, preferably of miniaturised construction, comprising a cylinder, a hollow cylindrical piston which is movable in the cylinder and provides a path for fluid therethrough, a high press chamber which is located in front of the piston inside the cylinder and which is supplied with fluid through said path, and an inlet valve in said fluid path which moves with the piston but is also capable of limited guided movement along the piston axis between a closed position in contact with a valve seat provided by the piston and an open position spaced from the valve seat, the valve member being so shaped and guided that it cannot rotate about any axis transverse to the piston axis such that a predetermined surface thereof engages the seat.

In U.S. Pat. 5,497,944, there is described and shown a similar device in which the check valve member is a ball. With such an arrangement, the ball can rotate during multiple operations. It has been found that wear and distortion under the high pressure involved can permanently deform the ball so that if a different part of its surf is used during sequential closing and sealing operations (because the ball is free to rotate about a transverse axis) there is a tendency for leakage to occur. This can be avoided by using the same surface of the valve member each time thus allowing bedding down to ensure the desired seal. In the preferred arrangement according to the invention, at least a major pare of the valve member is cylindrical and is guided in a chamber (which may, for example, be the pump chamber itself or may be part of the interior of the piston and the valve member cylinder has an end surface which co-operates with the valve seal provided by the piston. Another disadvantage of a ball valve which can be avoided using the invention is that the transverse area of the valve is necessarily considerably smaller than the diameter of the ball and thus the guide cylinder in which it moves; this leads to a reduction in the force applied by the valve member to the valve seat arising from fluid pressure generated during te pressure stroke (forward movement) of the piston. A high application force of the valve member is desirable to slightly elastically deform the valve member and and/or the valve seat to close any slight gaps between them.

In the specification which follows, the terms inlet and outlet side or inlet and outlet end are used in relation to the main direction of flow of the fluid within the device. The term fluid includes both gases and liquids but the present invention is mainly concerned with liquids.

The valve member is somewhat displaceable against the hollow piston but it moves substantially with the hollow piston.

The valve member is preferably uniaxially rotationally symmetrical in shape, e.g. it is a circular cylinder or a frustum. Its cross-section is somewhat smaller than the cross-section of the chamber in which the valve member is movably mounted. This is achieved by means of one or more channels preferably extending in the outer surface of the cylindrical valve member, or by a somewhat smaller diameter of the valve member in relation to the diameter of the chamber in which the valve member is movably mounted.

The valve member is guided in the chamber in which it is movably mounted; a cylindrical valve member can rotate about its axis as required, but its axis always remains parallel to the axis of the hollow piston. This produces a defined sealing surface at the inlet end of the valve member.

The distance over which the valve member can travel relative to the hollow piston is limited by a stop or stop means which holds the movable valve member together with the hollow piston.

In some embodiments of the invention wherein the stop is beyond the outlet end of the valve member, there may need to be at least one recess in the region of the outlet end of the valve member to enable the fluid to flow through between the stop and the valve member when the valve is open. The or each recess is located either in the valve member at the outlet end thereof or in the stop in the hollow piston.

In the position where the valve member abuts on the stop of the hollow piston, the valve is opened. In the position where the valve member abuts on the defined sealing surface, the valve is closed.

A valve member arranged inside the hollow piston has virtually no friction against the inner wall of the hollow piston. A valve member arranged ed directly in front of the end of the hollow piston may possibly rub against the wall of the main pump cylinder of the device. In this case, the valve is actively closed and opened as the hollow piston moves, on account of the friction between the valve member and the cylinder wall.

The cylinder preferably consists of plastics and the hollow piston of metal or plastics. The material for the valve member is selected, in terms of its hardness, to complement the hardness of the material for the hollow piston and may be metal, ceramics, glass, gemstone, plastics or elastomer. The valve member is preferably manufactured in one piece.

When the fluid is sucked in, the high pressure chamber is connected to the fluid supply by means of the hollow piston. During the intake stroke of the hollow piston the fluid flows through the hollow piston and past the valve member into the high pressure chamber of the cylinder. During the exhaust stroke of the hollow piston the valve seat is scaled in high pressure tight manner against the defined sealing sure of the valve member.

The device according to the invention for producing high pressure in a fluid is connected to the fluid supply at its inlet end. The high pressure chamber is connected to another device into which or through which the fluid is conveyed under high pressure. The hollow piston or the cylinder is attached to a drive which brings about relative movement between the hollow piston and cylinder and which applies the force required to generate the high pressure.

In the first embodiment, the cylindrical valve member may be guided and mounted in axially movable manner directly in front of the end of the hollow piston, the diameter of the valve member being substantially equal to the internal diameter of the cylinder. On the outside, near its outlet end, the hollow piston has an encircling, preferably turned or shaped groove as a stop member, into which a plurality of snap hooks on the valve member engage. Instead of the groove, the hollow piston may have at its outlet end a shaped taper with an encircling, outwardly funnel-shaped edge. The outer diameter of the hollow piston at its outlet end is greater than the base diameter of the groove and less than the diameter of the cylinder. Instead of the encircling groove, the outlet end of the hollow piston may be provided on the outside, at several, preferably 2 diametrically opposed points, with flattened areas which form a step to act as a stop means. The flat end of the hollow piston provides a valve seat cooperating with a defined flat sealing surface on the inlet side of the valve member. The outer edge at the end of the hollow piston may be chamfered.

In the second embodiment, the cylindrical valve member may be guided and movably mounted directly in front of the end of the hollow piston, the diameter of the valve member being substantially equal to the internal diameter of the cylinder. The end of the hollow piston is shaped inwardly to provide an inturned lip and acts as a stop means. On the valve member is mounted a coaxial, undercut, mushroom-shaped peg the snap hooks of which engage behind the shaped edge of the hollow piston. The defined sealing surface which extends around the peg rests on the outlet end of the piston on the edge of the lip.

In te third embodiment, the preferably cylindrical valve member may be mounted so as to be fully movable inside the hollow piston. The outlet end of the hollow piston has an internal diameter greater than the internal diameter of the remainder of the hollow piston. The length of this widened portion of the hollow piston is somewhat greater than the length of the valve member. The diameter of the valve member is substantially equal to the inner diameter at the widened end of the hollow piston. The outlet end of the hollow piston is shaped inwardly to form a lip either over its entire periphery or over a part of its periphery and acts as a stop which holds the valve member inside the hollow piston. The base of the widened portion which forms the valve seat may be flat or conical. A fluid flow recess in the outlet side the valve member may, for example, take the form of a stepped channel. A fluid flow recess in the stop may be constructed, for example, as an indentation in the lip edge.

In a variant of this embodiment, the valve member may be arranged totally inside the hollow piston at the inlet end thereof. The stop will then be located at the outlet end of the widened portion and the defined sealing surface will then be on the shaped edge at the inlet end of the hollow piston.

In the fourth embodiment, the hollow piston consists of a thin-walled tube which is shaped at its end projecting in the cylinder and is provided with an encircling constriction at the end of the space allowed for the valve member. The cylindrical valve member is guided and movably mounted in the pace between the shaped edge and the encircling constriction. Another thick-walled tube may be pushed into the inlet end of the hollow piston, its outer diameter being equal to the inner diameter of the hollow piston, and this thick-walled tube further being fixedly connected to the hollow piston and preferably extending approximately up to the encircling constriction in the hollow piston. The thick-walled tube acts as a displacement member and makes it easier for the fluid to be sucked into the high pressure chamber virtually without pressure being applied. The thick-walled tube is preferably made of plastics.

In a it of this embodiment, the valve member may be mounted fully inside the hollow piston at the inlet end thereof. The stop is then located at the encircling constriction a the defined sealing surface is located at the shaped edge at the inlet end of the hollow piston.

In the fifth embodiment, the hollow piston comprises a thin-walled tube which contains a thick-walled tube the outer diameter of which is equal to the inner diameter of the hollow piston, and which is fixedly connected the hollow piston. The thick-walled tube functions as a displacement body and makes it easier for the fluid to be sucked in virtually without pressure being applied.

The inlet end of the hollow piston is widened. At the widened end, the hollow piston is fixedly connected to a closure member the outer diameter of which is greater than the outer diameter of the widened inlet end of the hollow piston. The closure member contains a depression which is open on its side facing the widened end of the hollow piston. In the base of the depression is an opening acting as an inlet for the fluid. The base of the depression may be conical or fat; it forms the defined sealing surface.

The valve member is arranged in the depression in the closure member; it is guided so as to be axially movable in the depression. The external diameter of the valve member is smaller than the internal diameter of the depression, but preferably greater than the internal diameter of the hollow piston in that part of it which projects into the cylinder. The valve member may contain, at its outlet end, at least one recess through which the fluid flows into the high pressure chamber during the intake stroke of the hollow piston.

The stop for the valve member is preferably the end of the displacement body which projects into the widened portion of the hollow piston, or—if the, end of the displacement body is located in the unwidened portion of the hollow piston—the transition from the unwidened portion of the hollow piston into the widened inlet end thereof.

The hollow piston with the widened inlet end preferably consists of metal. The displacement body and closure member are preferably made of plastics. The valve member may be made of plastics or metal.

Of particular significance is the use of the device according to the invention for producing high pressure in a fluid in an atomiser (nebulizer) for propellant-free spraying of the fluid.

According to another aspect of the invention, there is provided an atomiser for spraying a fluid, consisting of an upper housing part, a pump housing, a nozzle, a blocking mechanism, a spring housing, a spring and a supply container, characterised by a pump housing fixed in the upper housing part which has at one end a nozzle member with the nozzle, a hollow piston with valve member, a drive flange in which the hollow piston is secured and which is located in the upper housing part, a blocking mechanism located in the upper housing part, a spring housing with the spring located therein, which is rotatably mounted by means of a rotary bearing on the upper housing part, a lower housing part which is fitted onto te spring housing in the axial direction.

Other aspects of the invention are set out in the independent claims but variations and combinations of particular features therein can be made without departing from the scope of the invention. Certain preferred features are defined in the subclaims Further preferred features of the atomiser will now be described. The atomiser is preferably a metered dose inhaler.

The hollow piston with valve member preferably corresponds to one of the devices according to the invention mentioned hereinbefore. It projects partially into the cylinder of the pump housing and is mounted in axially movable manner in the cylinder. The hollow piston with valve member exerts a pressure of 5 to 60 MPa (about 50 to 600 bar), preferably 10 to 60 MPa (about 100 to 600 bar) on the fluid at its high pressure end at the moment of release of the spring.

The nozzle in the nozzle member is preferably microstructured, ie. produced by microtechnology. Microstructured nozzle members are disclosed, for example, in U.S. Pat. No. 5,472,143, the entire contents of which are incorporated herein by reference.

The nozzle member consists, for example, of two plates of glass and/or silicon firmly joined together, of which at least one plate has one or more microstructured channels which connect the nozzle inlet end to the nozzle outlet end. At the nozzle outlet end is at least one circular or non-circular opening less than or equal to 10 $\mu$m in size. Size in this connection refers to hydraulic diameter. Hydraulic diameters in this type of apparatus are generally less than 100 micrometres preferably 1–20 micrometres.

The directions of spraying of the nozzles in the nozzle member may run parallel to one another or may be inclined relative to one another. In a nozzle member having at least two nozzle openings at the outlet end, the directions of spray may be inclined relative to one another at an angle from 20 to 160°, preferably at an angle from 60 to 150°. The directions of spraying meet in the vicinity of the nozzle openings.

In the pump housing, a non-return valve with or without spring bias may be provided between the nozzle opening and the high pressure chamber of the cylinder. This non-return valve closes off the high pressure chamber in the resting state of the atomiser, protects the fluid from the entrance of air and may if necessary prevent volatile components of the fluid from evaporating out of the pump housing. The non-return valve opens automatically as soon as the pressure of the fluid in the high pressure chamber exceeds a minimum value and the current of fluid is created; it closes automatically as soon as the current of fluid is exhausted. The non-return valve may be, for example, a ball valve. It way also consist of a flexible plate which is clamped on one side and rests like a flap on the outlet end of the high pressure chamber. In another embodiment It may consist of a disk of preferably flexible material, clamped all the way round, pierced by a pin. The pierce hole allows the current of fluid to pass through to the nozzle as soon as the pressure in the fluid exceeds a minimum value. After the current of fluid is exhausted, the pin hole closes up again.

The valve member is preferably mounted at the end of the cylinder facing the nozzle member.

The blocking or latching mechanism has a spring, preferably a cylindrical helical compression spring, as a store for mechanical energy. The spring acts on the driven flange as a jumping member the movement of which is determined by the position of a block member. The path of travel of the driven flange is precisely defined by an upper and lower stop. The spring is preferably tensioned by an external torque via a force stepping-up device, eg. a helical sawtooth trust cam, the force being generated as the upper housing part rotates counter to the spring housing in the lower housing part. In this case, the upper housing part and the driven flange comprise a single or multiple sawtooth wedge arrangement.

Mechanisms of this general type are disclosed in U.S. Pat. No. 4,260,082 and GB Application 2291135 the entire contents of both of which are incorporated herein by reference.

The blocking member with engaging blocking surfaces is arranged in an annular configuration around the driven flange. It consists, for example, of a plastics or metal ring which in one form is inherently radially resiliently deformable. The ring is arranged in a plane at right angles to the atomiser axis. After the biassing of the spring, the blocking surfaces of the blocking member move into the path of the driven flange and prevent the spring from being released. The blocking member is actuated by a button. The actuating button is connected or coupled to the blocking member in order to actuate the blocking mechanism the actuating button is pushed parallel to the plane of the ring, preferably into the atomiser; the deformable ring is thereby deformed in the plane of the ring to release the flange for movement by the spring.

The preferred blocking member and spring are described and shown in German Patent Application 195432267 and filed by Microparts but assigned to Boehringer Ingelheim International GmbH. The entire contents of this application is incorporated herein by reference.

The atomiser optionally contains a mechanical counter comprising a screw threaded spindle which is mounted on the spring housing. The axis of the spindle extends in the region of the outer surface parallel to the axis of the atomiser. The spindle is mounted, in the region of its ends, by means of a rotary bearing on the spring housing. The spindle has teeth at the end closest to the upper housing part. On the edge of the upper housing part is at least one cam which engages in the tooth at the end of the spindle when the two housing parts are rotated relative to one another. A slider with rotation prevention means is mounted on the spindle and engages its threads.

The preferred counter is described and shown in German Patent Application 195 49 033,9 dated Dec. 28, 1995 and filed by Microparts but assigned to Boehringer Ingelheim International GmbH. The entire contents of this application is incorporated herein by reference.

The lower housing part is pushed axially over te spring housing and covers the mounting, the drive of the spindle and the storage container for the fluid. The position of to slider is visible through a recess in te lower housing part and can be read off on a sale, eg. on the lower housing part.

When the atomiser is actuated to upper housing part is rotated relative to the lower housing part the lower housing part carrying the spring housing with it. The spring meanwhile is compressed and biassed by means of the helical thrust cam, and the blocking mechanism engages automatically. The angle of rotation is preferably a whole-number fraction of 360°, eg. 180°. At the same time as the spring is biassed, the driven part in the upper housing part is moved a certain distance, the hollow piston is retracted inside the cylinder in te pump housing, as a result of which some of the fluid is sucked out of the storage container into the high pressure chamber in front of the nozzle.

By means of the gears, which consist of a piston on one end of the spindle and a rack or racks on the edge of the upper housing part, the relative movement of the two housing parts is picked up and converted into a rotary movement of the spindle and displacement of the slider on the spindle. On each actuation of the atomiser, the slider is moved a certain distance along the spindle.

The position of the slider indicates what proportion of the fluid to be atomised has already been taken from the storage container and how much is still available. The slider on the spindle can be reset if necessary by means of a resetting lug.

If desired, a plurality of (preferably collapsible) replaceable storage containers holding the fluid which is to be atomised can be inserted into the atomiser one after another and used. The storage container is not-pressurised or substantially not pressurised. The pressure of the fluid in the storage container is in any case substantially lower than the pressure generated in the high pressure chamber by the medically operated atomiser. The storage container contains, for example, a fluid containing a drug.

A suitable container with a dimensionally stable outer part and an inner part collapsible as the liquid therein is removed as disclosed in U.S. Pat. No. 5,316,135, the entire contents of which are incorporated herein by reference.

The atomising process is started by gently pressing the actuating button. The blocking mechanism then opens up a path for the driven pan to move. The biassed spring pushes the piston into the cylinder of the pump housing. The fluid leaves the nozzle of the atomiser in spray form.

The components of the atomiser are made of a material which is suitable for the function. The housing of the atomiser and, insofar as function allows, other parts are preferably made of plastics, eg. by injection moulding. For medicinal purposes, physiologically acceptable materials are used.

The atomiser according to the invention is used, for example, for propellant-free production of medicinal aerosols. An inhalable aerosol with a mass average particle (droplet) size of about 5 $\mu$m can be produced thereby. These small particles (average size less than 12 $\mu$m) are necessary for penetration right down into the lungs. The amount discharged is preferably about 15 microlitres.

The following active substance are mentioned by way of example of pharmaceutical compositions in the form of aqueous or ethanolic solutions, depending on the solubility of the active substance: berotec, berodual, flunisolide, atrovent, salbutamol, budesonide, combivent, tiotropium, oxivent and suitable peptides.

The solutions may also contain pharmaceutically acceptable excipients.

The preferred device according to the invention for producing high pressure in a fluid and the preferred atomiser containing this device have the following advantages:

The device contains a valve which operates without any auxiliary force (produced by a spring) and closes as a result of the flow resistance of the fluid on the valve member or as a result of the friction on the cylinder wall.

The valve is tight against a pressure generally above 3 MPa (30 bar).

The valve member is made in one piece; it is easy to manufacture and assemble.

The valve closes very rapidly owing to the short distance travelled by the valve member to reach the defined sealing surface.

The valve has a high sealing action.

As a result of the guiding of the uniaxially rotationally symmetrical valve member, a defined sealing surface is produced which is high pressure tight through a very large number of cycles of movement of the hollow piston.

The dead space of the high pressure chamber can be kept extremely small.

The atomiser can be operated safely and easily even by untrained persons, both to bias the spring and to actuate the atomising process.

The atomiser works without propellant gas and is therefore environmentally friendly.

The storage container for the fluid is not pressurised or substantially not pressurised.

The movement of the blocking member is automatically coupled, by a simple method, to the rotary movement for biassing the spring.

In a preferred embodiment the atomiser consists of low-wear purely mechanical components and operates reliably over long periods.

Owing to the defined abutments for the driven part the metering of the fluid is very accurate.

The atomiser can be manufactured cheaply and assembled easily.

The mechanical counter is automatically advanced as the atomiser is actuated; it is uncritical of tolerance, easy to assemble and operates safely and reliably.

The counter is inaccessible when the atomiser is used properly and cannot be falsified by accident The counter can be adapted to any number of releases of fluid from the storage container and to different overall numbers of storage containers to be used with one atomiser.

The counter is integrated in the atomiser and does not take up any additional space.

No substances can pass from the counter into the substance which is to be atomised.

Preferred embodiments of the invention will now be described by way of example with reference to the drawings in which.

The various embodiments of the pump device have already been described above in general terms but these descriptions will now be supplemented with further description with reference to the drawings.

Figure 1A:
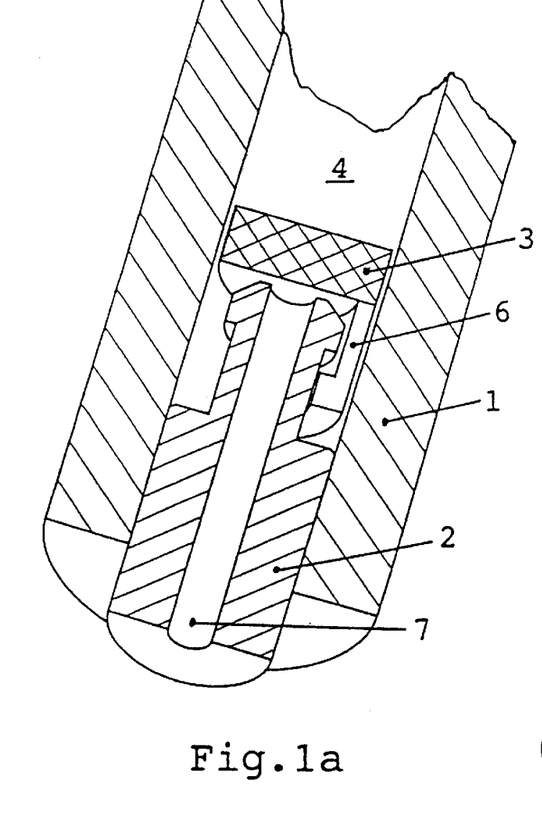
FIGS. 1a, 1b and 1c are respectively a longitudinal section of a fast embodiment of a pump for producing high pressure in a fluid according to the invention, an oblique view of its hollow piston and an oblique view of its valve member.

FIG. 1a shows a longitudinal section, viewed obliquely, through the first embodiment of the device according to the invention for producing high pressure in a fluid. In the cylinder (1) is the hollow piston (2) with the coaxial bore (7) and the valve member (3) in the partly open position of the valve. Between the bottom of the valve member (3) and the end of the cylinder is the high pressure chamber (4). The high pressure chamber is closed off by another component (not shown). Mounted on the hollow piston, outside the cylinder, is a device (not shown) by means of which the hollow piston can be displaced inside the cylinder.

Figure 1B:
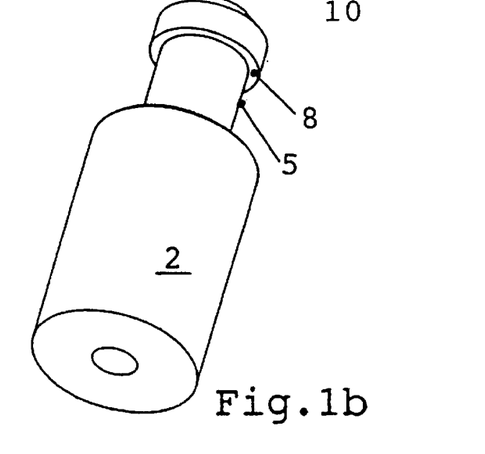

FIG. 1b shows the hollow piston (2) viewed obliquely. The end of the hollow piston facing the valve, member is provided with a groove (S) which is bounded, at its end facing the valve member, by a rectangular section annular land forming a step (8) the diameter of which is less than the external diameter of the hollow piston (2) and greater than the base diameter of the groove. The front edge at the end of the hollow piston may be chamfered.

Figure 1C:
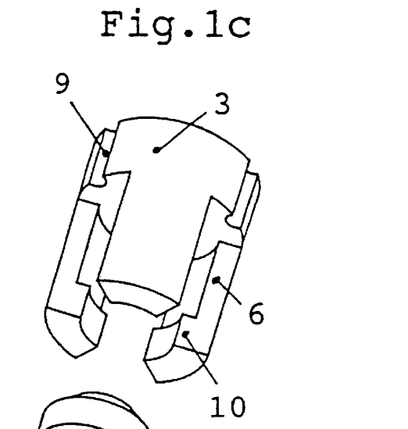

FIG. 1c shows the valve member (3) viewed obliquely. It has, for example, three channels (9) on its outer sub to facilitate fluid flow when the valve is open. Mounted on the valve member (3), on its side facing the hollow piston, are, for example, three snap hooks (6) the width of which, in the direction of the circumference of the valve member, is less than a third of this circumference. The snap hooks (6) are shorter in the axial direction than the length of the, for example, grooved end of the hollow piston.

During assembly, the valve member (3) is placed on the end of the hollow piston (2), and the hook (10) slide into the groove. The hollow piston together with the valve member is then pushed into the cylinder.

When the valve is open, the inner edge of the hooks (10) abut on the step (8). When the valve is closed, the base of the valve member (3) facing the hollow piston fits tightly on the end of the hollow piston (2) which as the defined sealing surface.

In order to take in the fluid, the hollow piston is lifted partly out of the cylinder, whereupon the valve automatically opens. The fluid flows through the bore (7) in the hollow piston and past the valve member into the high pressure chamber (4). In order to expel the fluid, the hollow piston (2) is pushed into the cylinder (1), whereupon the valve closes automatically, virtually instantly, and high pressure is generated in the fluid.

Figure 2A:
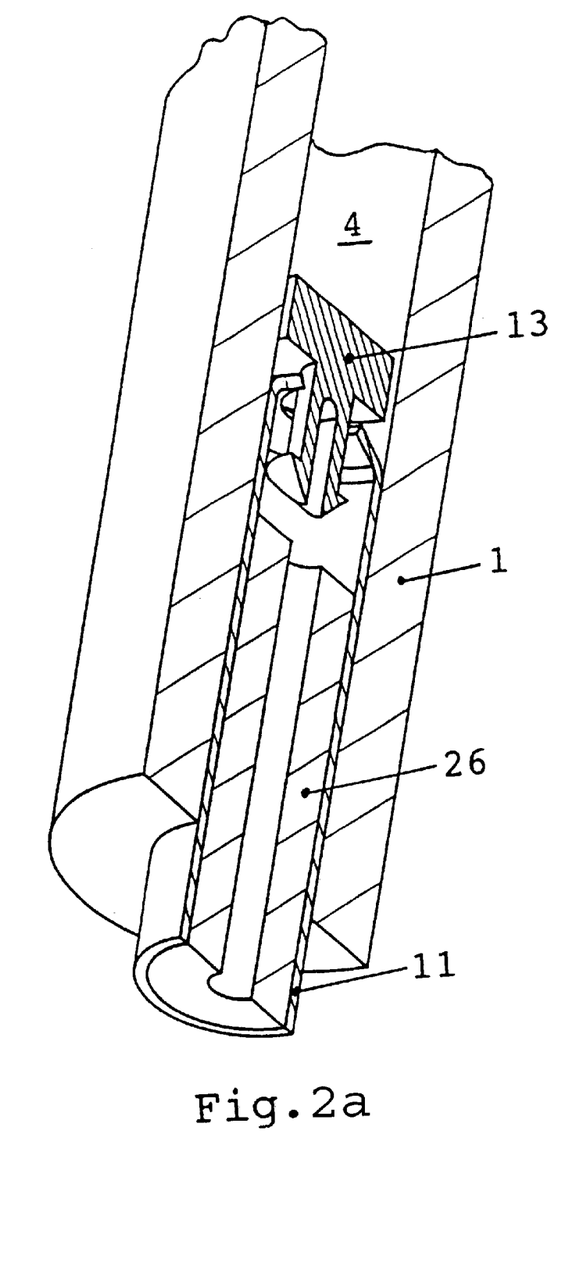
FIGS. 2a, 2b and 2c are similar views of a second embodiment.

FIG. 2a shows the second embodiment of the device according to the invention for producing high pressure in a fluid as a longitudinal section viewed obliquely. In the cylinder (1) is the hollow piston (11) and the valve member (13) in the partly open position of the valve.

Figure 2B:
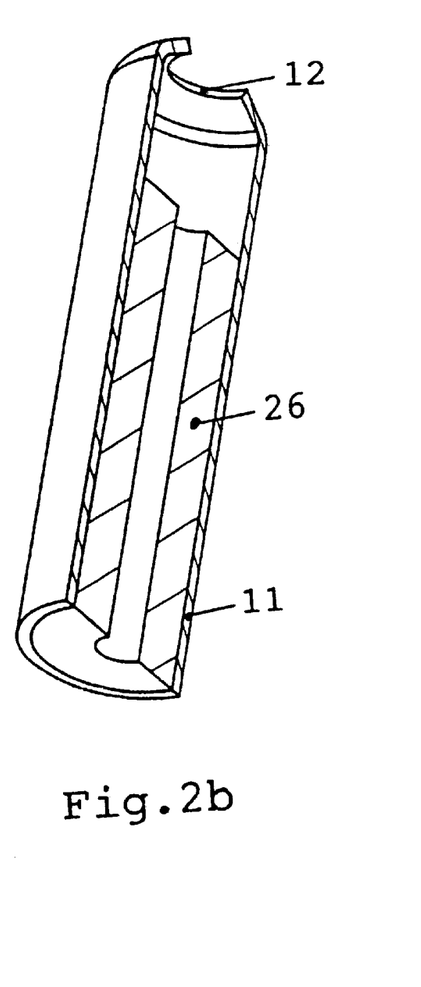

FIG. 2b shows a longitudinal section trough the hollow piston (11) with the shaped outlet end (12) of the hollow piston. A displacement body (26) way be fixedly located in the hollow piston.

Figure 2C:
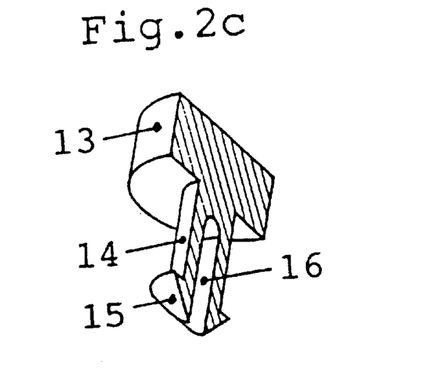

FIG. 2c shows the valve member (13) as a longitudinal section viewed obliquely. Mounted on the valve member is a coaxial, undercut peg (14) the projecting end of which engages behind the shaped edge (12) of the hollow piston. The end (15) of the peg facing the hollow piston may be chamfered. The peg may have an indentation or bore (16) extending in the axial direction and possibly longitudinal slots extending upwards from the end (15) thus forming snap hooks so that the peg can be pushed into the shaped end of the hollow piston, thereby engaging behind the shaped edge.

Figure 3A:
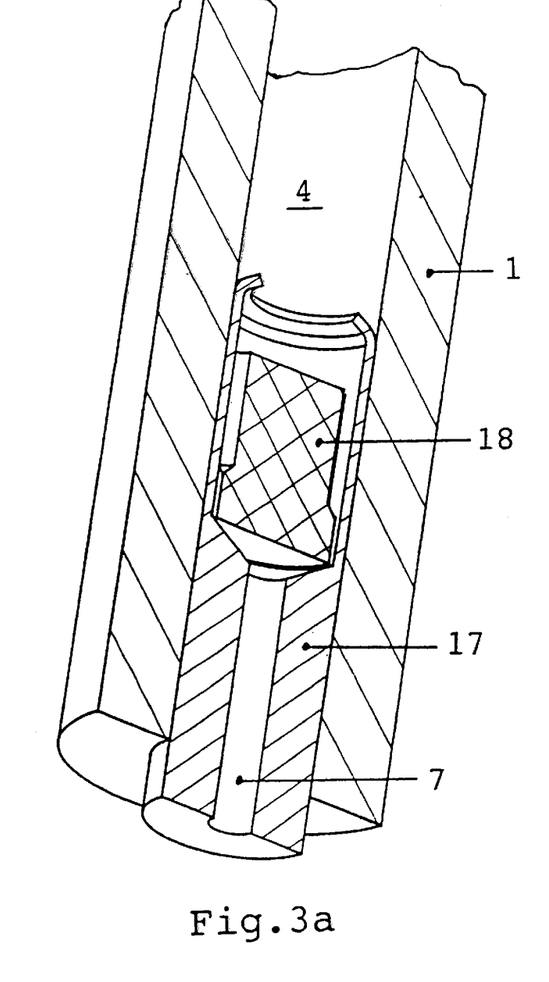
FIGS. 3a, 3b and 3c arm similar view of a third embodiment.

FIG. 3a shows the third embodiment of the device according to the invention for producing high pressure in a fluid in longitudinal section viewed obliquely. In the cylinder (1) is the hollow piston (17) and the valve member (18) In he closed position of the valve.

Figure 3B:
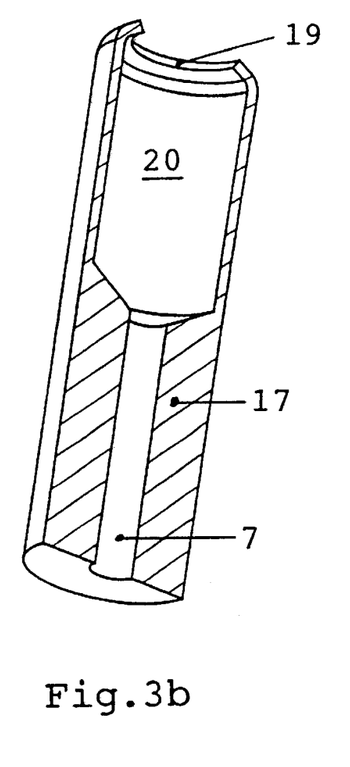

FIG. 3b shows a longitudinal section viewed obliquely through the hollow piston (17) with the shaped end (19). At the outlet end of the hollow piston is the widened portion (20) in which the valve member (18) is guided and mounted in axially movable manner. The inlet end of the widened portion (20) is chamfered or flat.

Figure 3C:
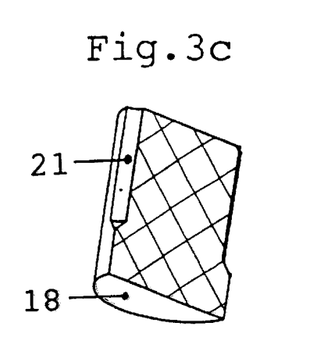

FIG. 3c shows the cylindrical valve member (18) in longitudinal section viewed obliquely. Both ends of the valve member are planar and are located perpendicularly to the axis of the valve member. The valve member (18) contains, for example, four stepped channels or flats (21) on its outer surface to facilitate fluid flow past the shaped end (19), i.e. the inturned lip, when the valve is open, the ends of the channels (21) being radially inward of the lip. The edge of the valve member (18) which abuts on the inclined base of the hollow chamber (20) may be chamfered.

The diameter of the valve member (18) is less than the diameter of the widened portion (20) so that the valve member (18) can move virtually without friction in the widened portion (20).

For assembly, the valve member (18) is pushed into the widened portion (20) before the outlet end (19) of the hollow piston is shaped.

Figure 4A:
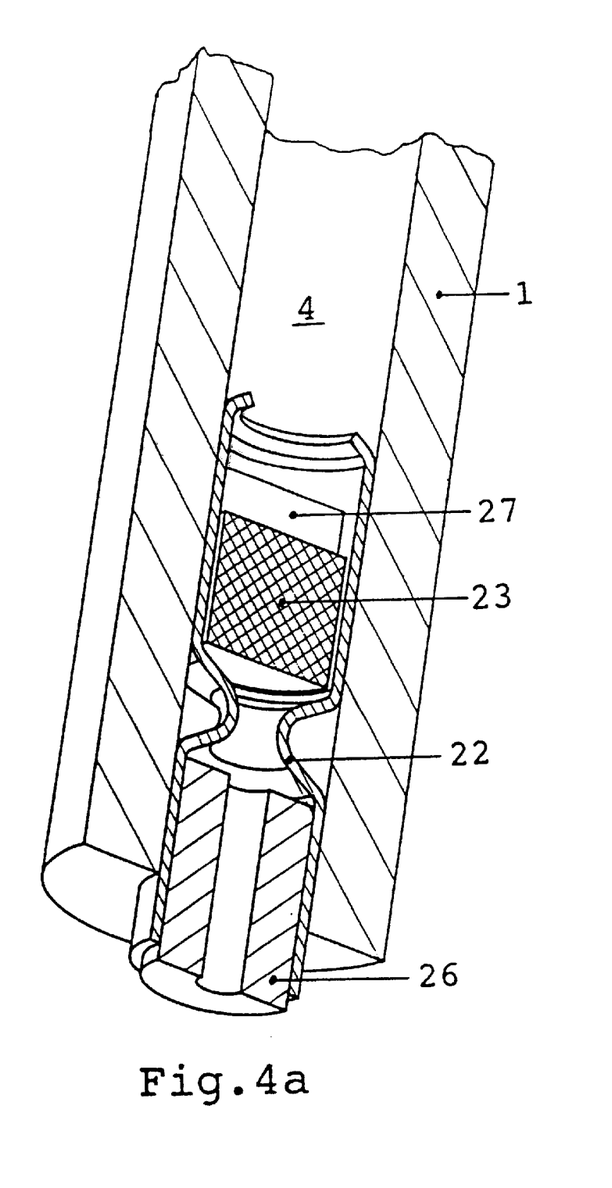
FIGS. 4a, 4b and 4c are similar views of a fourth embodiment.

FIG. 4a shows the fourth embodiment of the device according to the invention for producing high pressure in a fluid in longitudinal section viewed obliquely. In the cylinder (1) are the hollow piston (22) and the valve member (23) in te closed position of the valve. The diameter of the valve member is less than the inner diameter of the hollow piston.

Figure 4B:
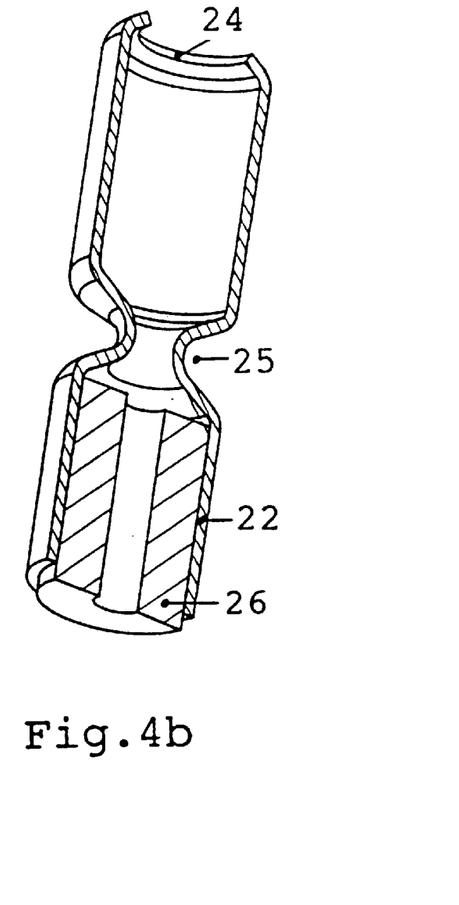

FIG. 4b shows a longitudinal section, viewed obliquely, through the hollow piston (22) with the shaped outlet end (24) forming an inturned lip and the encircling constriction (25). The thick-walled tube (26) acting as the displacement body may be pushed into the hollow piston (22) and secured therein.

Figure 4C:
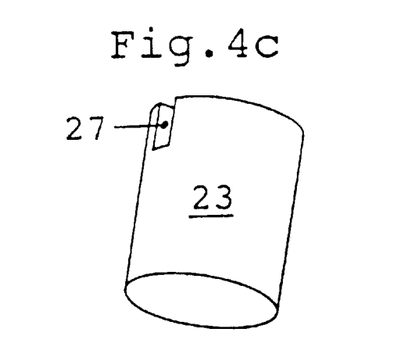

FIG. 4c shows the valve member (23) in oblique view. At the outlet end of the valve member is a radially extending indentation (27) in the form of a transverse slot to facilitate fluid flow when the valve is open.

Figure 4D:
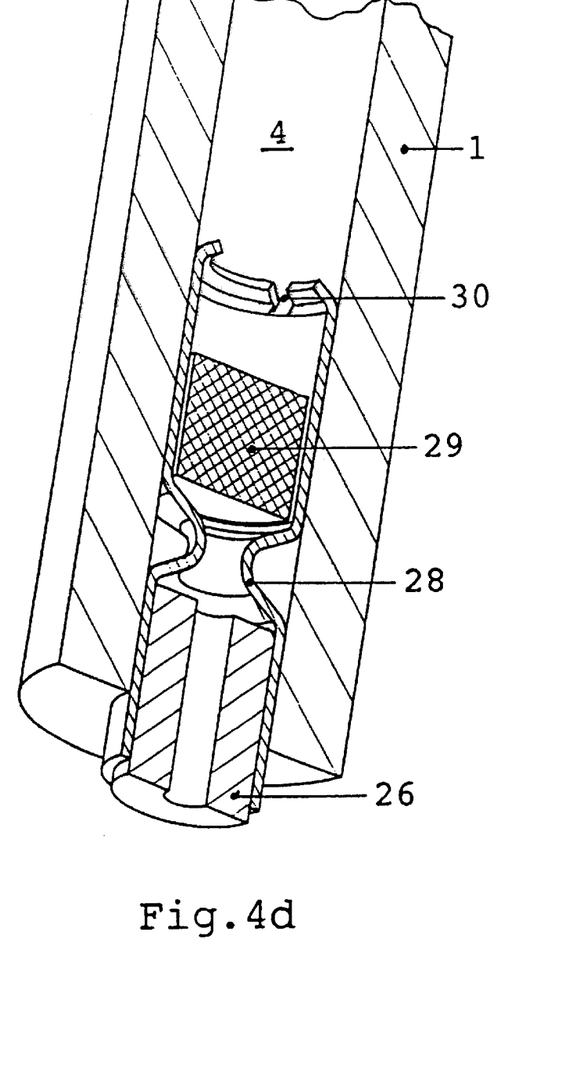
FIGS. 4d, 4e and 4f are similar views of a modification of the fourth embodiment.

FIG. 4d shows an alternative to the fourth embodiment in longitudinal section, viewed obliquely. In the cylinder (1) is the hollow piston (28), optionally with the displacement body (26), with the valve in the closed position. The diameter of the valve member (29) is less than the internal diameter of the hollow piston.

Figure 4E:
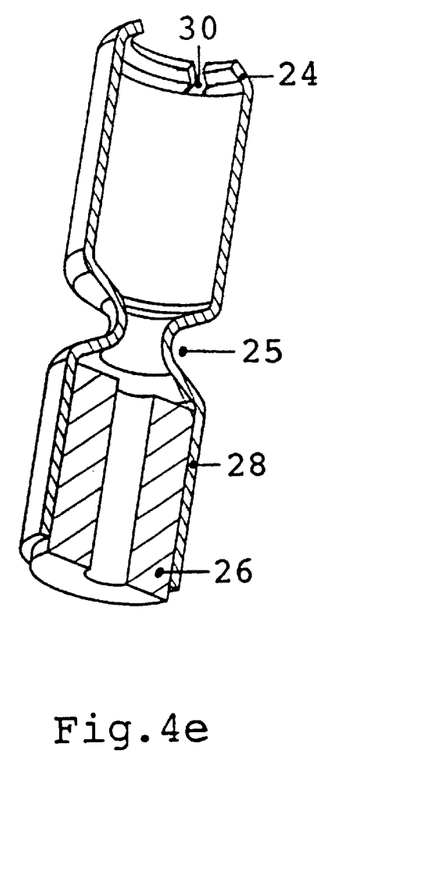

FIG. 4e shows a longitudinal section, viewed obliquely, through the hollow piston (28) with the shaped outlet end (24) and the encircling constriction (25). At least one indentation (30) in the form of a recess or notch is provided on the shaped outlet end (24) to facilitate fluid flow when the valve is open. Instead of the indentation there may be a convexity.

Figure 4F:
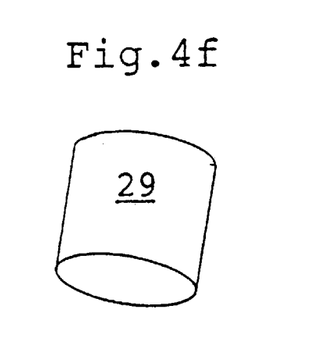

FIG. 4f shows the valve member (29) in oblique view. In this case, the valve member is a straight cylinder with no recesses.

Figure 5:
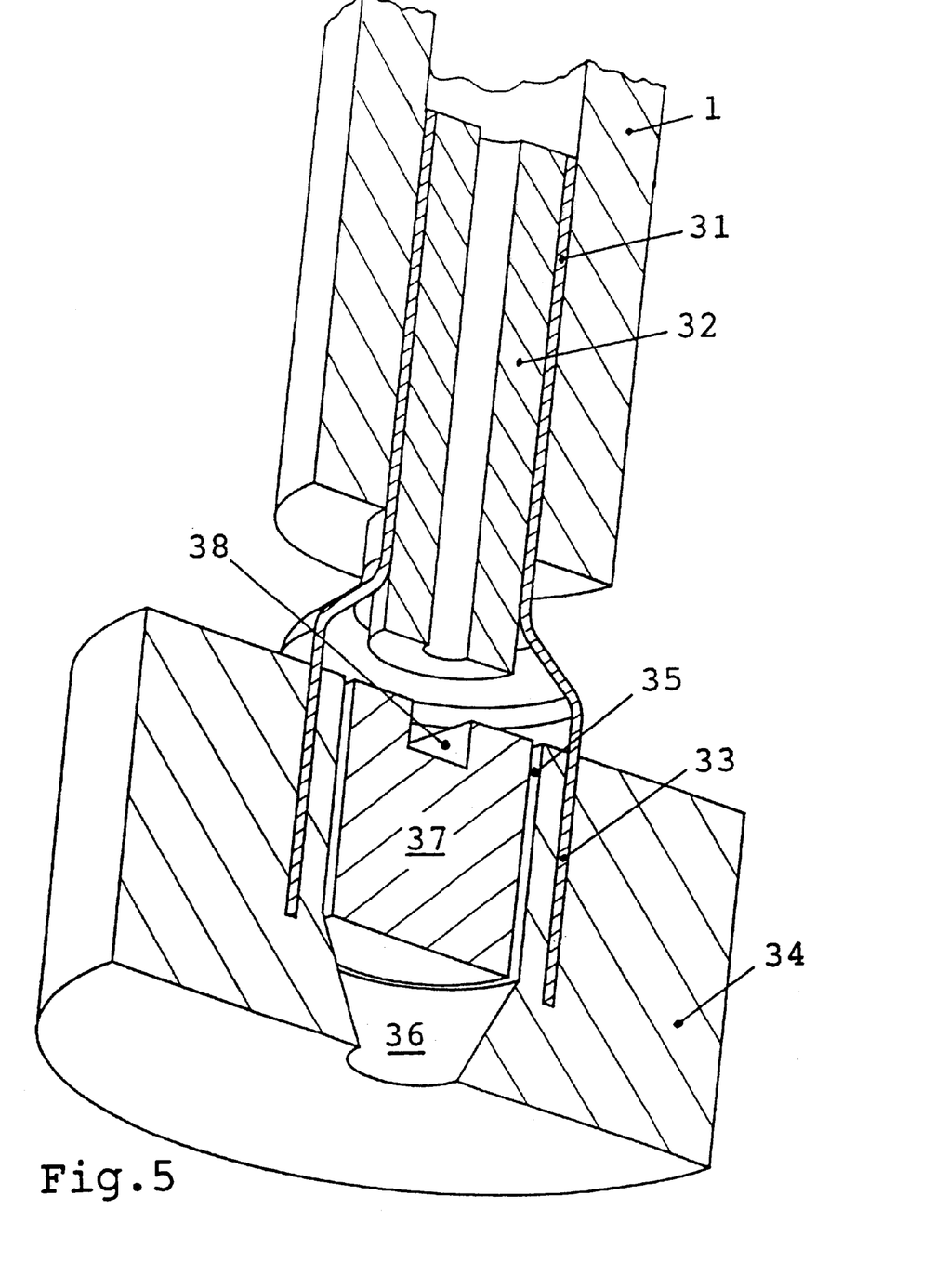
FIG. 5 is a longitudinal section of a fifth embodiment.

FIG. 5 shows the fifth embodiment of the device according to the invention for producing high pressure in a fluid, in longitudinal section and viewed obliquely. In the cylinder (1) is the hollow piston (31) which contains the displacement body (32). Mounted on the cylindrically widened inlet end (33) of the hollow piston is the closure member (34) with the depression (35) and bore (36). In the indentation is the guided, axially movable valve member (37) which may be provided at its outlet end with a slot (38) as recess.

The embodiments of the device according to the invention for producing high pressure in a fluid shown in FIGS. 2a to 5 work in the same way as has already been explained with Fence to FIG. 1a.

Figure 6A:
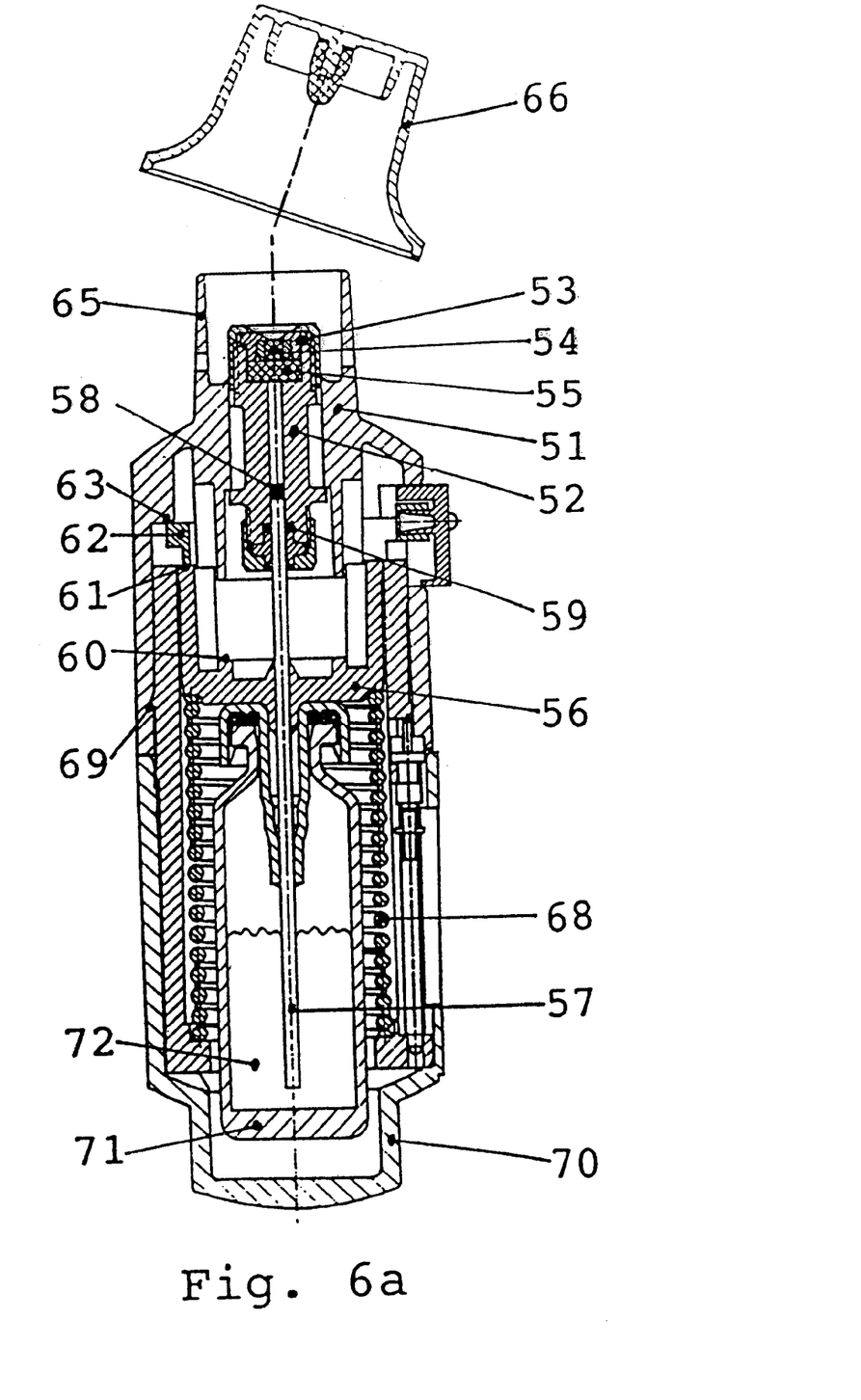
FIGS. 6a and 6b are longitudinal cross-sections of a metered dose inhaler according to the invention in different operative conditions.
Figure 6B:
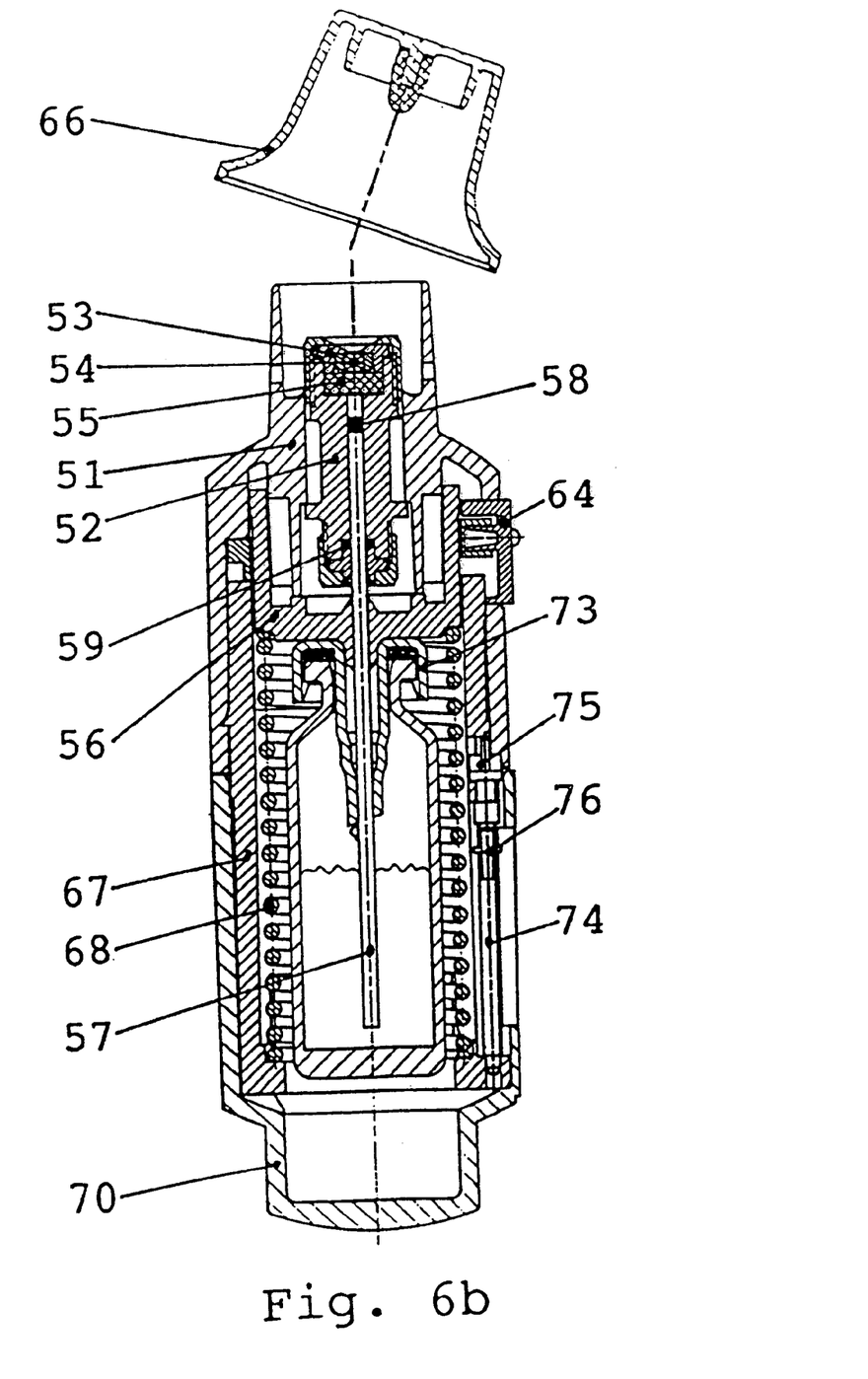

FIG. 6a shows a longitudinal section through the preferred atomiser described in detail above with the spring biassed and FIG. 6b shows a longitudinal section through the atomiser with the spring released.

The upper housing part (51) contains the pump housing (52) on the end of which is mounted the holder (53) for the atomiser nozzle. This holder is preferably as described in German Patent Application P19536303.3-51 of Oct. 4, 1995 (and a parallel PCT application being filed simultaneously herewith in the joint names of Boehringer Ingelheim International GmbH and the inventors) the entire contents of which are incorporated herein by reference. In the holder is the nozzle member (54) and a filter (55). The hollow piston (57) fixed in the cup-shaped drive flange (56) of the blocking mechanism (62) partly projects into the cylinder of the pump housing. At its end the hollow piston carries the valve member (58). The hollow piston is sealed off by the seal (59). Inside the upper housing part is the annular abutment (opposite annular ridge (60) on the flange) on which the flange rests when the spring is released. On the axial end of the cup-shaped driven flange is the abutment (61) by which the driven flange is held when the spring is biased. After the biassing of the spring, the generally annular blocking member (62) moves between the abutment (61) and a support (63) in the upper housing part, either because of its own elasticity or (when it is more rigid) by virtue of an external spring (not shown). The actuating button (64) is connected to the blocking member and can either move it bodily or deform it so that it releases the abutment (61). The upper housing part terminates in the mouth piece (65) and is closed off by the protective cap (66) which can be fitted thereon.

The spring housing (6) with compression spring (68) is rotatably mounted on the upper housing part by means of the snapping lug (69) and rotary bearing. The lower housing part (70) is pushed over the spring housing and rotates with it to operate the helical sawtooth cam drive (not show) for cocking the atomiser (moving it from the FIG. 6b position to the FIG. 6a condition). Inside the spring housing is the replaceable storage container (71) for the fluid (72) which is to be atomised. The storage container is fitted with a stopper (73) through which the hollow piston project into the storage container and dips its end into the fluid.

Mounted in the outer surface of the spring housing is the spindle (74) for the mechanical counter. At the end of the spindle facing the upper housing part is the drive pinion (75). The slider (76) sits on the spindle.

The embodiments shown in the drawings may be varied further. The components may be used together in a manner other than that shown in the drawings.

EXAMPLE 1

Miniaturised Device for Producing High Pressure for a Medicinal Atomiser

The valve area of a medicinal atomiser according to FIG. 1a consists of a cylinder made of polybutylene-terephthalate with an internal diameter of 1.6 mm and an external diameter of 5 mm. The high pressure chamber is closed off by a nozzle carrier plate. In this plate is a nozzle 20 µm in diameter and the nozzle channel is 2 mm long.

A metal hollow piston with an external diameter of 1.59 mm and a bore 0.35 mm in diameter is pushed into the cylinder. The hollow piston can be pushed 50 mm Into the cylinder and its stroke is 12 mm long. The hollow piston has an encircling turned groove 4 mm wide with a base diameter of 0.75 mm. The groove is bounded by a 4.0 mm long step with a diameter 1.15 mm. The outer edge of turned end of the hollow piston is chamfered.

The valve member made of polybutyleneterephthlate consists of a 2 mm thick disk 1.59 mm in diameter and 3 snap hooks. Three semi-cylindrical channels 0.4 mm in are provided as recesses on the outer surface of the disk. The snap hooks project 6 mm from the disk and the inner edge of the hooks is 4.2 mm away from the disk. The valve member may thus be moved axially 0.2 mm relative to the hollow piston.

The delivery volume is 23.4 $mm^3$. The pressure in the fluid is about 32 MPa (320 bar).

This atomiser is used to atomise or nebulize liquid pharmaceuticals for medicinal aerosol therapy. The atomiser delivers the drug in the required dose on each actuation.

EXAMPLE 2

Miniaturised Device for Producing High Pressure for a Cosmetic Atomiser

The valve area of a cosmetic atomiser corresponding to FIG. 3*a* consists of a cylinder of polyetherether-ketone with an internal diameter of 2.5 mm and an outer diameter of 8 mm. The high pressure chamber is closed off by a nozzle carrier plate. In this plate is a nozzle 25 μm in diameter with a nozzle channel 2 mm long.

A hollow piston of reinforce plastic with an external diameter of 2.48 mm and a bore 0.5 mm in diameter is pushed into the cylinder. The hollow piston can be pushed 45 mm into the cylinder and its stroke is 24 mm. The hollow piston is drilled out to an internal diameter of 1.85 mm over a length of 5.0 mm at its outlet end. The base of the drilled-out chamber in the hollow piston is chamfered. The outlet end of the hollow piston is thermally deformed.

The valve member is a cylinder of polypropylene which is 3.0 mm high and 1.6 mm in diameter. Four stepped channels are provided as reseses in the outer surface. The valve member can be displaced axially about 0.5 mm inside the hollow piston.

The delivery volume is about 116 $mm^3$. The pressure in the fluid is about 3 MPa (30 bar).

This atomiser is used to atomise a hair spray.

What is claimed is:

1. A device for pressurizing fluid, comprising:

a cylinder;

a cylindrical hollow piston movable in said cylinder and providing a path for fluid therethrough, wherein an inlet end or an outlet end of said hollow piston includes a widened portion, an inner diameter of said widened portion being greater than the inner diameter of the remainder of said hollow piston, and wherein said inlet end or said outlet end includes an inwardly shaped edge;

a valve seal provided by said piston;

a high pressure chamber inside said cylinder; and a valve operating without any auxiliary force, said valve including, a uniaxially rotationally symmetrical valve member including a sealing surface at an inlet end of said valve member to cooperate with said valve seal, said valve member being guided inside said widened portion of said hollow piston, wherein the diameter of said valve member is less than said inner diameter of said widened portion and is greater than said inner diameter of the remainder of said hollow piston, such that said valve member does not extend into the remainder of said hollow piston, stop means provided at an outlet end of said widened portion to hold said valve member inside said hollow piston, a recess in said stop means or a recess or radially extending indentation in said valve member at an outlet end thereof, wherein said valve is closed when said valve member abuts said valve seal and said valve is open when said valve member abuts said stop means.

2. A device according to claim 1, wherein said sealing surface is an end surface of said valve member.

3. A device according to claim 1, wherein said high pressure chamber is located in front of said hollow piston.

4. A device according to claim 1, wherein said valve member is mounted in an axially movable manner.

5. A device according to claim 1, wherein at least a major part of said valve member is cylindrical.

6. A device according to claim 1, wherein said valve member is cylindrical.

7. A device according to claim 1, wherein said widened portion is disposed at said outlet end of said cylindrical hollow piston and said inwardly shaped edge is disposed at said outlet end of said hollow piston and comprises said stop means.

8. A device according to claim 1, wherein said widened portion is disposed at said inlet end of said hollow piston, said inwardly shaped edge is disposed at said outlet end of said hollow piston and comprises said stop means.

9. A device according to claim 1, further comprising:

an encircling constriction near said inwardly shaped edge of said hollow piston, wherein said valve member is guided and mounted in axially movable manner inside said hollow piston between said inwardly shaped edge and said encircling constriction; and a recess in the region of said outlet end of said valve member.

10. A device according to claim 9, wherein said inwardly shaped edge is disposed at said inlet end of said hollow piston and comprises said valve seal; and said encircling constriction is provided in the vicinity of said inwardly shaped edge at said inlet end of said hollow piston and comprises said stop means.

11. A device according to claim 9, wherein said inwardly shaped edge is disposed at said outlet end of said hollow piston and comprises said stop means.

12. A device according to claim 1, wherein said cylindrical hollow piston includes a first encircling constriction spaced apart from said outlet end of said hollow piston, said first encircling said constriction comprising said stop means, and a second encircling constriction between said first construction and said inlet end of said hollow piston, said second encircling constriction comprising said valve seal; and wherein said valve member is guided and mounted in axially movable manner between said first and second constrictions.

13. A device according to claim 12, further comprising a displacement body disposed at said inlet end of said hollow piston, said displacement body having an axially extending channel and being arranged in and fixedly connected to said hollow piston, said displacement body extending as far as said second encircling constriction.

14. A device according to claim 12, further comprising a displacement body disposed at said outlet end of said hollow piston, said displacement body having an axially extending channel and being mounted in and fixedly connected to said hollow piston, said displacement body extending as far as said first encircling constriction.

15. A device according to claim 1, wherein a said widened portion is disposed at said inlet end of said hollow piston and the device further comprises:

a tube disposed in the remainder of said hollow piston, a closure member disposed at said widened portion, said closure member connected to and containing a flat or conical depression with a bore, and a slot provided at said outlet end of said valve member as a recess or a notch.

* * * * *